United States Patent
Mandelstam-Manor et al.

(10) Patent No.: US 8,226,237 B2
(45) Date of Patent: Jul. 24, 2012

(54) APPARATUS AND METHOD FOR MONITORING THE POSITION OF A SUBJECT'S HAND

(75) Inventors: Yair Mandelstam-Manor, Tel-Aviv (IL); Gideon Hanoch Benyamini, Ramat Hasharon (IL); Omer Rafaely, Tel-Aviv (IL); Yair Alster, Tel-Aviv (IL)

(73) Assignee: Reichert, Inc., Depew, NY (US)

( * ) Notice: Subject to any disclaimer, the term of this patent is extended or adjusted under 35 U.S.C. 154(b) by 302 days.

(21) Appl. No.: 11/860,584

(22) Filed: Sep. 25, 2007

(65) Prior Publication Data

US 2008/0079902 A1 Apr. 3, 2008

Related U.S. Application Data

(60) Provisional application No. 60/847,650, filed on Sep. 28, 2006.

(51) Int. Cl.
*A61B 3/02* (2006.01)
(52) U.S. Cl. ......................................... 351/222; 600/595
(58) Field of Classification Search .................. 351/222; 600/595
See application file for complete search history.

(56) References Cited

U.S. PATENT DOCUMENTS

| | | | |
|---|---|---|---|
| 4,349,250 A | 9/1982 | Gelius | |
| 4,634,243 A | 1/1987 | Massof et al. | |
| 4,798,456 A | 1/1989 | Enoch et al. | |
| 4,822,162 A | 4/1989 | Richardson et al. | |
| 4,995,717 A | 2/1991 | Damato | |
| 5,061,060 A | 10/1991 | Aulhorn et al. | |
| 5,157,717 A * | 10/1992 | Hitchcock | 379/93.19 |
| 5,412,561 A | 5/1995 | Rosenheim et al. | |
| 5,463,431 A | 10/1995 | Suzuki et al. | |
| 5,506,633 A | 4/1996 | Sperling | |
| 5,539,482 A | 7/1996 | James et al. | |
| 5,565,949 A | 10/1996 | Kasha, Jr. | |
| 5,589,897 A | 12/1996 | Sinclair et al. | |

(Continued)

FOREIGN PATENT DOCUMENTS

WO    WO 03/070089    8/2003

(Continued)

OTHER PUBLICATIONS

Enoch Jay M. et al., "Hyperacuity Perimetry: Assessment of Macular Function Through Ocular Opacities", Arch Ophtalmol, vol. 102(8), Aug. 1984, pp. 1164-1168.

(Continued)

*Primary Examiner* — Max Hindenburg
*Assistant Examiner* — Renee Danega
(74) *Attorney, Agent, or Firm* — Hodgson Russ LLP

(57) ABSTRACT

A system for delivering a touch sensitive screen task to a subject includes a touch sensitive display for presenting visual stimuli to a subject and for providing a response of the subject, hand position monitoring unit(s) for receiving input indicative of the position of a hand of the subject and for providing output signals representing said position and a controller/processor unit operatively coupled to the touch sensitive display unit and to the hand position monitoring unit(s) for receiving output signals from the hand position monitoring unit(s) and for processing the output signals to control the displaying of the visual stimuli on the touch sensitive display unit. A method for operating the system includes receiving from the subject signals representing a response of the subject to visual stimuli, receiving signals indicative of the position of the subject's hand and processing the signals to control the presenting of visual stimuli.

16 Claims, 10 Drawing Sheets

U.S. PATENT DOCUMENTS

| | | | |
|---|---|---|---|
| 5,864,384 A | 1/1999 | McClure et al. | |
| 5,883,692 A | 3/1999 | Agonis et al. | |
| 5,892,570 A | 4/1999 | Stevens | |
| 5,946,075 A | 8/1999 | Horn | |
| 6,027,217 A | 2/2000 | McClure et al. | |
| 6,033,076 A | 3/2000 | Braeuning et al. | |
| 6,260,970 B1 | 7/2001 | Horn | |
| 6,406,437 B1 | 6/2002 | Zur et al. | |
| 6,513,931 B1 | 2/2003 | Torrey et al. | |
| 6,520,640 B1 | 2/2003 | Binnun | |
| 6,527,391 B1 | 3/2003 | Heijl et al. | |
| 6,572,229 B2 | 6/2003 | Wei | |
| 6,578,966 B2 | 6/2003 | Fink et al. | |
| 6,585,376 B1 | 7/2003 | Matsumoto | |
| 6,656,131 B2 | 12/2003 | Alster et al. | |
| 6,688,746 B2 | 2/2004 | Malov | |
| 6,742,894 B2 | 6/2004 | Stewart | |
| 7,170,500 B2 * | 1/2007 | Canova, Jr. | 345/173 |
| 7,220,000 B2 * | 5/2007 | Alster et al. | 351/224 |
| 7,275,830 B2 | 10/2007 | Alster et al. | |
| 2002/0042580 A1 | 4/2002 | Alster et al. | |
| 2003/0223038 A1 * | 12/2003 | Alster et al. | 351/211 |
| 2006/0244735 A1 * | 11/2006 | Wilson | 345/173 |
| 2007/0121070 A1 | 5/2007 | Alster et al. | |

FOREIGN PATENT DOCUMENTS

| | | |
|---|---|---|
| WO | WO 2004/098477 | 11/2004 |

OTHER PUBLICATIONS

Wall, Michael and Sadun, Alfredo A.. "Threshold Amsler Grid Testing: Cross-Polarizing Lenses Enhance Yield" Arch Ophtalmol., vol. 104 (4), Apr. 1986, pp. 520-523.

Stuart L. Fine and The Macular Photocoagulation Study Group, "Early Detection of Extrafoveal Neovascular Membranes by Daily Central Field Evaluation", Ophtamol. 92(5), May 1985, 603-609.

Vasudevan Lakshminarayanan et al., "Quantification of Metamorphopsia Using Hyperacuity Techniques", Optometry and Vision Science, vol. 68, No. 12, Dec. 1991, pp. 942-945.

Michael J. Tolentino et al. "Visual Field Deficits in Early Age-Related Macular Degeneration", Vision Res., vol. 34, No. 3, pp. 409-413, Feb. 1994.

Reginald J. Ariyasu et al., "Sensitivity, Specificity and Predictive Values of Screening Tests for Eye Conditions in a Clinic-Based Population", Ophtamology, vol. 103, No. 11, Nov. 1996, pp. 1751-1760.

Michael M. Slavin, "The Use of the Red Amsler Grid and Red-Green Lenses in Detecting Spurious Paracentral Visual Fields Defects", American Journal of Opthalmology, vol. 103, No. 3, Part 1, Mar. 1987, pp. 338-339.

Wall, Michael and May, Donald R. "Threshold Amsler Grid Testing in Maculopathies", Ophtalmol.94(9), Sep. 1987, pp. 1126-1133.

* cited by examiner

APPARATUS AND METHOD FOR MONITORING THE POSITION OF A SUBJECT'S HAND

CROSS-REFERENCE TO RELATED US APPLICATIONS

This application claims priority from and the benefit of U.S. Provisional Patent Application Ser. No. 60/847,650 filed on Sep. 28, 2006 entitled "APPARATUS AND METHOD FOR MONITORING THE POSITION OF A SUBJECT'S HAND", incorporated herein by reference in its entirety.

FIELD OF THE INVENTION

This invention relates in general to the field of systems for performing visual testing and more particularly to systems and methods for monitoring the position of a hand of a subject performing a touch screen task.

BACKGROUND OF THE INVENTION

Methods and systems for performing patient or subject testing using presentation of visual stimuli or test patterns on a screen or display device are well known in the art. For example U.S. Pat. No. 6,656,131 to Alster et al., Published International Patent Application, Publication Number WO/2003/070089 and Published International Patent Application Publication Number WO/2004/098447, All of which are incorporated herein by reference in their entirety, disclose systems and methods for detecting and diagnosing eye disease by displaying visual stimuli to a subject and recording and analyzing the subject's responses. Often, such systems employ a touch sensitive screen (touch screen). Visual stimuli are presented to the subject on the touch screen. The subject may provide a response to a presented test stimulus by touching the touch sensitive screen.

In some of the above exemplary systems, the response of the subject to the presentation of a visual stimulus may be of two types. The subject may ignore the current stimulus and wait for the next stimulus, or the subject may touch the screen at a location that depends on the stimulus type, and then wait for the next stimulus. Two problems may arise with this type of task: (1) Immediately before and during the time that the stimulus is presented on the touch screen, the subject's hand must not obstruct the subject's view of the touch screen. (2) While the subject is responding, the program that displays the visual stimulus on the touch screen must delay the presentation of the next visual stimulus until the subject completes the task (i.e., touches the screen and repositions his hand such that it does not obstruct his view of the screen), before a new stimulus can be triggered.

FIGS. 1A-1E are schematic diagrams illustrating part of an exemplary prior art system employing a touch screen task presented to a subject within a test and an exemplary sequence of steps occurring within such a test. In FIG. 1A, typically, one of the subject's hands is used to perform the task (it is noted that for the sake of clarity of illustration only the hand and the eye of the subject are illustrated in FIGS. 1A-1E). The subject's hand used for performing the task is referred to as the marking hand 100 hereinafter. When the test is performed, the marking hand 100 is at rest, and the subject's eye 105 is observing a touch screen 110, while the subject is waiting for a visual stimulus to be displayed on the touch screen 110. The touch screen 110 is suitably coupled to a computer 115. The marking hand 100 may hold a stylus pen 120 for facilitating precise pointing to a specific location on the touch screen 110. At the time immediately before and during the presentation of a test stimulus on the touch screen 110, it is required that no obstacle obstructs the visual field 125 that extends from the tested eye 105 to the touch screen 110 (as schematically illustrated by the dotted lines in FIG. 1A). In FIG. 1B, a program that runs on the computer 115 displays a visual stimulus 130 on the touch screen 110, and from this time onward the program waits for the subject to respond to the presentation of the visual stimulus 130. If the subject chooses to ignore the stimulus 130 (FIG. 1C), after a predefined time, the program enables a new cycle, and the presentation of a new visual stimulus is triggered. If the subject chooses to respond to the stimulus 130 (as illustrated in FIG. 1D), the subject touches the touch screen 110 with the stylus pen 120. At this time the marking hand 100 is raised, and this may obstruct the visual field 125 of the subject. Thus it may be advantageous that the program does not present the next stimulus to the subject until the marking hand 100 is lowered such that its does not obstruct the visual field 125 of the subject, as illustrated in FIG. 1C and FIG. 1E.

Thus, there is a need for providing the system and the program controlling the operation of the system with information regarding the position of the subject's hand, as well as with information indicating whether the subject is responding to the presentation of the stimulus.

SUMMARY OF THE INVENTION

There is therefore provided a system for delivering a touch sensitive screen task to a subject. The system includes a touch sensitive display unit for presenting visual stimuli to the subject and for providing responses of the subject to at least some of the visual stimuli, at least one hand position monitoring unit for receiving input indicative of the position of a hand of the subject and for providing output signals representing the position and a controller/processor unit coupled to the touch sensitive display unit and to the at least one hand position monitoring unit for receiving the output signals from the at least one hand position monitoring unit and for processing at least the output signals to control the displaying of the visual stimuli on the touch sensitive display unit.

Furthermore, in accordance with an embodiment of the system, the at least one hand position monitoring unit is selected from a mechanical hand position monitoring unit, an electromechanical hand position monitoring unit, an ultrasonic hand position hand position, a stationary switching unit, a hand held switching unit, a switching mechanism, an electromechanical switching mechanism, an electro-optical switching mechanism, a magnetic switching mechanism, an optical switch, an ultrasonic hand position monitoring unit, a radio frequency based hand position monitoring unit, an infra-red proximity sensing based hand position monitoring unit, a motion detecting device, a passive infra-red sensor based motion detecting device, a video camera based motion detecting device, a mechanical sensor, a magnetic sensor a capacitive sensor a proximity sensor, a passive motion sensor, an active motion sensor, an intrusion detecting sensor, an electro-optical sensor an electromechanical sensor, an electromagnetic sensor, an infra-red sensor a microwave sensor, a Doppler radar based sensor, a magnetostrictive material based sensor, and any combinations thereof.

Furthermore, in accordance with an embodiment of the system, the at least one hand position monitoring unit includes at least one switch. The switch is selected from a pushbutton switch, a latching switch, an optical switch, an electro-optical switch, a mechanical switch, an electromechanical switch, a magnetic switch and any combinations thereof.

Furthermore, in accordance with an embodiment of the system, the at least one hand position monitoring unit includes two hand position monitoring units including a first hand position monitoring unit usable for monitoring the position of the right hand of a right handed user and a second hand position monitoring unit usable for monitoring the position of the left hand of a left handed user.

Furthermore, in accordance with an embodiment of the system, the touch sensitive display unit is a touch sensitive display unit of a computer and the first hand position monitoring unit and the second hand position monitoring unit are selected from position monitoring units attached to the computer, position monitoring units attached to the display unit and position monitoring units which are selected regions of the touch sensitive display unit.

Furthermore, in accordance with an embodiment of the system, the at least one hand position monitoring unit is a hand held positioning/marking unit including a marking portion for marking on the touch sensitive display unit.

Furthermore, in accordance with an embodiment of the system, the output signals of the at least one hand position monitoring unit(s) are communicated to the controller/processor unit by communicating means selected from communication wires for connecting the at least one hand position monitoring unit and the controller/processor unit, and wireless communication devices.

Furthermore, in accordance with an embodiment of the system, the wireless communication devices are selected from wireless transmitters, wireless receivers, wireless transceivers, IR wireless transmitters, infra-red wireless receivers, infra-red transceivers, Ultrasonic wireless transmitters, ultrasonic wireless receivers, ultrasonic wireless transceivers, radio-frequency receivers, radio frequency transmitters, radio frequency transceivers, Bluetooth wireless receivers, Bluetooth wireless transmitters, Bluetooth wireless transceivers and any combinations thereof.

Furthermore, in accordance with an embodiment of the system, the hand position monitoring unit includes a platform configured for providing an output signal when a hand of the user is positioned on the platform.

Furthermore, in accordance with an embodiment of the system, the controller/processor unit is configured for presenting the visual stimuli to the subject upon receiving position signals indicative that a hand of the subject does not visually obstruct the visual field of the subject.

Furthermore, in accordance with an embodiment of the system, the controller/processor unit is configured for presenting the visual stimuli to the subject upon receiving position signals indicative that a hand of the subject does not block the subject's view of the touch sensitive display unit.

There is also provided a method for controlling the delivering of visual stimuli to a subject. The method includes the steps of presenting to the subject visual stimuli on a touch sensitive display unit, receiving from the subject, through the touch sensitive display unit, signals representing responses of the subject to at least some of the visual stimuli, receiving position signals indicative of the position of a hand of the subject and processing at least the position signals to control the timing of presenting of the visual stimuli to the subject.

Furthermore, in accordance with an embodiment of the method, the step of receiving position signals comprises the step of presenting said visual stimuli to said subject upon receiving position signals indicative that a hand of the subject does not visually obstruct the visual field of said subject.

Furthermore, in accordance with an embodiment of the method, the step of receiving position signals includes the step of presenting the visual stimuli to the subject upon receiving position signals indicative that a hand of the subject does not block the subject's view of the touch sensitive screen.

Furthermore, in accordance with an embodiment of the method, the position signals are output by at least one hand position monitoring unit selected from a mechanical hand position monitoring unit, an electromechanical hand position monitoring unit, an ultrasonic hand position hand position, a stationary switching unit, a hand held switching unit, a switching mechanism, an electromechanical switching mechanism, an electro-optical switching mechanism, a magnetic switching mechanism, an optical switch, an ultrasonic hand position monitoring unit, a radio frequency based hand position monitoring unit, an infra-red proximity sensing based hand position monitoring unit, a motion detecting device, a passive infra-red sensor based motion detecting device, a video camera based motion detecting device, a mechanical sensor, a magnetic sensor a capacitive sensor a proximity sensor, a passive motion sensor, an active motion sensor, an intrusion detecting sensor, an electro-optical sensor an electromechanical sensor, an electromagnetic sensor, an infra-red sensor a microwave sensor, a Doppler radar based sensor, a magnetostrictive material based sensor, and any combinations thereof.

Furthermore, in accordance with an embodiment of the method, the position signals are selected from wirelessly received position signals and position signals received through wires.

Furthermore, in accordance with an embodiment of the method, the step of receiving position signals indicative of the position of a hand of the subject is selected from receiving position signals indicative of the position of the right hand of the subject and receiving position signals indicative of the position of the left hand of the subject.

Furthermore, in accordance with an embodiment of the method, the step of presenting the first step of receiving, the second step of receiving and the step of processing are performed in the order recited hereinabove.

Furthermore, in accordance with an embodiment of the method, the position signals are caused by an active action of said subject.

Furthermore, in accordance with an embodiment of the method, the active action includes the intentional activating of a switching mechanism by the subject.

There is also provided a method for controlling the delivering of visual stimuli to a subject. The method includes the steps of resenting to the subject visual stimuli on a touch sensitive display unit, receiving from the subject, through the touch sensitive display unit, signals in response to at least some of the visual stimuli, receiving signals indicating that a hand of the subject does not block the subject's view of the touch sensitive screen and presenting to the user the next visual stimulus only after receiving the signals indicating that a hand of the subject does not block the subject's view of the touch sensitive screen.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Disclosed herein are systems and methods for monitoring the position of the hand of a subject when the subject is performing a touch screen task in response to a visual stimulus presented on a touch screen.

Figure 1:
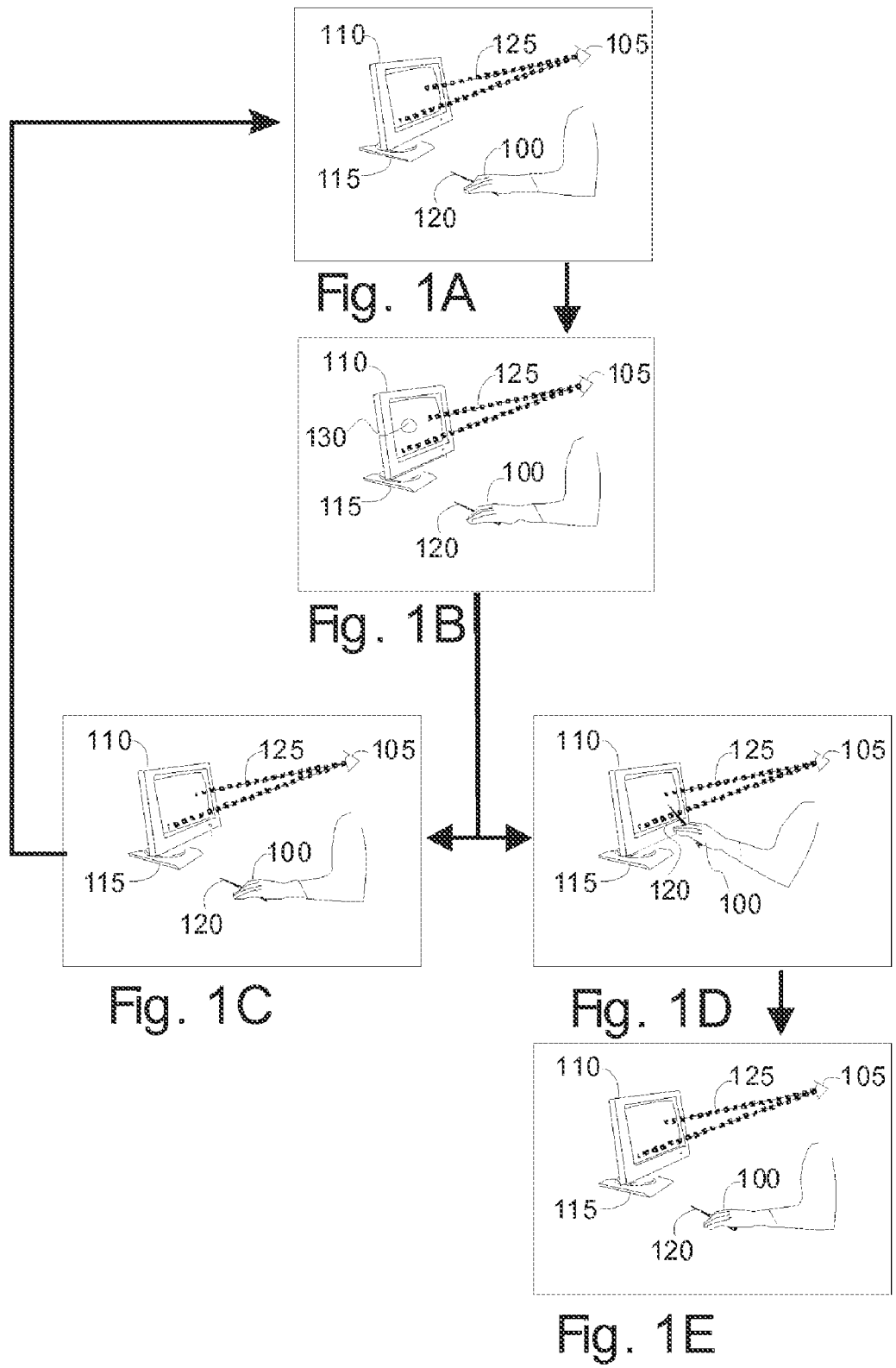
FIGS. 1A-E are schematic diagrams illustrating various interactions of a subject with a prior art testing system including a touch sensitive screen.
Figure 2:
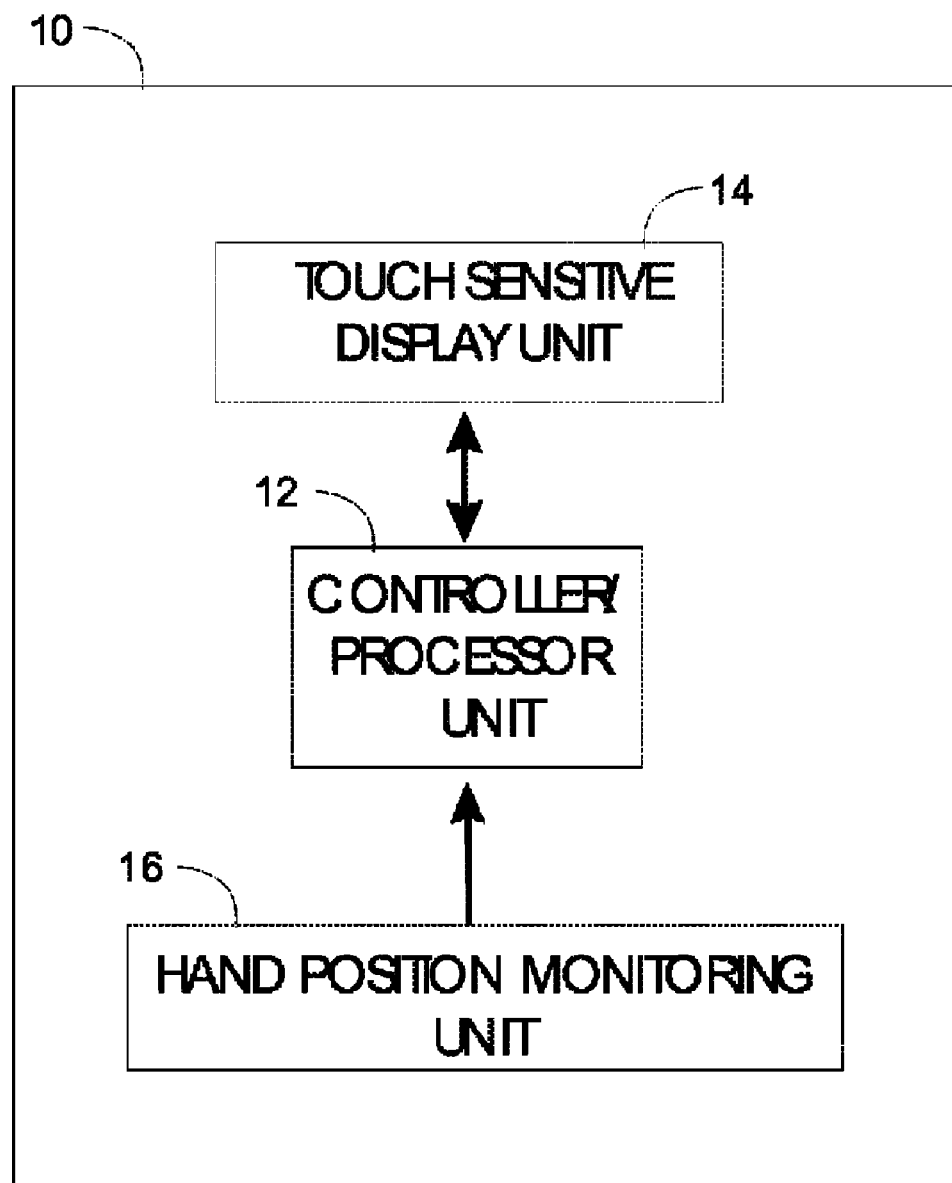
FIG. 2 is a schematic block diagram illustrating the general structure of a system with hand position monitoring for performing touch screen tasks, in accordance with an embodiment of the present invention.

Reference is now made to FIG. 2 which is a schematic block diagram illustrating the general structure of a system for performing a touch screen task with hand position monitoring, in accordance with a first embodiment.

The system 10 includes a controller/processor unit 12 suitably coupled to a touch sensitive display unit 14. The controller/processor unit 12 may be any suitable controller and/or processor unit known in the art, including but not limited to, a computer, a personal computer, a laptop computer, a desktop computer, a server, a networked computer, a workstation, a microprocessor, a microcontroller, a digital signal processor (DSP), a computer connected to a local area network (LAN), a computer connected to a wide area network (WAN), a computer connected to a private virtual network (PVN), a minicomputer, a mainframe computer, and the like. In non-limiting exemplary embodiments, the controller/processor unit 12 may be part of the computer 115 of FIGS. 1A-E, or may be implemented in accordance with any of the embodiments disclosed in U.S. Pat. No. 6,656,131 to Alster et al., Published International Patent Application, Publication Number WO/2003/070089 and Published International Patent Application Publication Number WO/2004/098447, incorporated herein by reference in their entirety.

The touch sensitive screen 14 may be any known type of touch sensitive screen which is capable of presenting visual stimuli to a subject and of providing output signals to the controller/processor unit 12 when touched by a subject or by an object held by a subject (such as but not limited to a stylus, a light pen, a pointing device, and the like).

The system 10 also includes a hand position monitoring unit 16 which is suitably coupled to the processor/controller unit 12. The hand position monitoring unit 16 may be any type of device known in the art that can provide an output signal representing information about the position of the hand of a subject (not shown in FIG. 2) to the processor/controller unit 12. The type of the signal(s) provided by the hand position monitoring unit 16 may differ depending on the particular type of the hand position monitoring unit 16 being used. The details of construction and operating of the system 10 are disclosed in detail hereinafter with respect to specific exemplary embodiments of the system 10.

Generally, the output signal(s) provided by the hand position monitoring unit 16 is received by the processor/controller unit 12 and may be used to determine the timing of displaying stimuli to the subject. For example, if the output signal(s) (or, alternatively, the lack of an output signal) indicates that the subject has not returned the marking hand 100 to the rest position, the processor/controller unit 12 may delay the presentation of a new stimulus on the touch sensitive display unit 14. Similarly, if the output signal (or, alternatively, the lack of an output signal) indicates that the subject's marking hand 100 (see FIGS. 1A and 3A) is at the rest position (and therefore is not obstructing the subject's field of view, and may also indicate that the subject has finished responding to a previously presented stimulus), the processor/controller unit 12 may present the next stimulus (if appropriate) on the touch sensitive display unit 14.

Figure 3A:
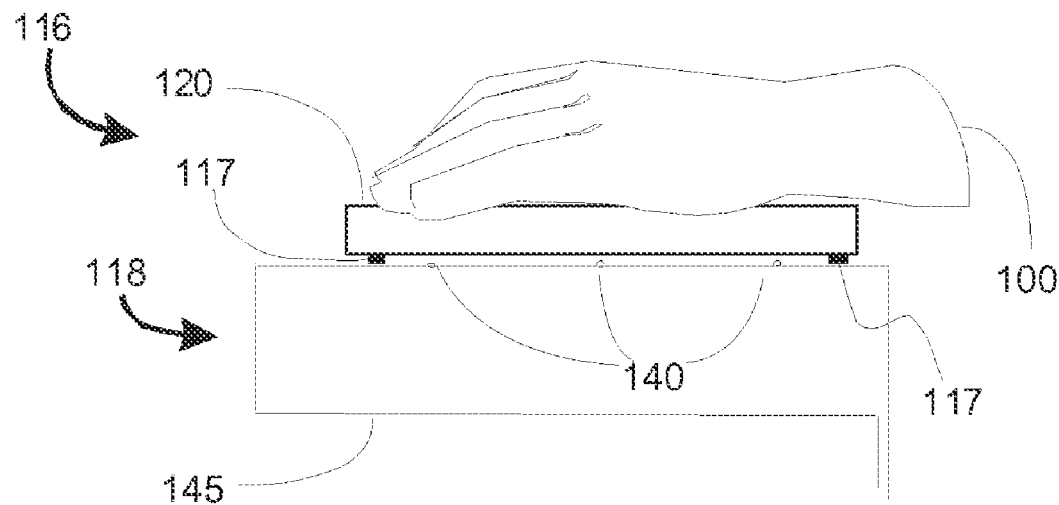
FIGS. 3A and 3B are schematic diagrams illustrating two different states of an electro-mechanical hand position monitoring device suitable for use in the system of FIG. 2.
Figure 3B:
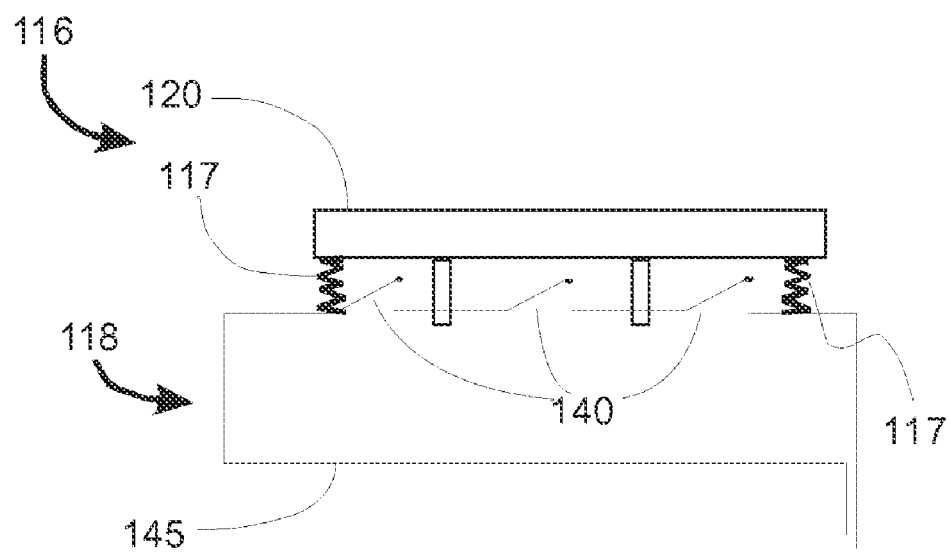

Reference is now made to FIGS. 3A and 3B which are schematic diagrams illustrating two different states of an electromechanical hand position monitoring device suitable for use in the system of FIG. 2. The hand position monitoring device 116 is implemented as a switching device having a platform 120. The platform 120 is coupled to a switching device 118. The switching device 118 includes a plurality of switches 140. The switches 140 may be mechanical switches or optical switches or any other suitable type of switches known in the art. In accordance with one possible embodiment, the switches 140 are electro-mechanical switches connected in series (as illustrated in FIG. 3B) and are part of an electrical circuit 145 that is connected to a port of the computer 115 (see FIG. 1A-E), however, any other types of switch (es) may be used as is known in the art.

When the marking hand 100 of the subject rests on the platform 120, the weight of the marking hand 100 exerts pressure on the platform 120, and the switches 140 close the electrical circuit 145. The resulting electrical current is transmitted to the computer 115. This output current signals that the subject is ready for the next cycle, since the hand 100 does not obstruct the visual field 125 (not shown) of the subject. A visual stimulus may then be presented on the touch sensitive display unit 14 (not shown in FIGS. 3A-3B) of the system 10. The processor/controller 12 processes the output signal(s) received from the switching device 118 and then triggers the display of the visual stimulus on the touch sensitive display unit 14. Thus, the presentation of the stimulus is triggered by passive relaxation of the marking hand on the platform 120. The platform 120 is positioned such as to ensure that the marking hand 100 does not obstruct the visual field of the subject.

When training the subject in taking the test using the hand position monitoring unit illustrated in FIGS. 3A-3B, the subject may be trained to place the marking hand 100 on the platform 120 at the beginning of the test and to return the marking hand 100 to the platform 120 after touching the touch sensitive display unit in response to a presented stimulus.

Turning to FIG. 3B, when the subject raises the marking hand 100 to mark a location on the touch screen 115, the platform 120 is pushed by returning springs 117 and moves upwards such that switches 140 open. The electrical circuit 145 is now an open circuit, and the electrical current in the circuit 145 drops to zero. This zero current indicates that the subject may be in the process of making a response, and that the marking hand 100 may (possibly) be obstructing the visual field 125. The test program running in the computer 115 waits until the subject returns the marking hand 100 to the platform 120, (as signaled by current flow in the circuit 145) and only then triggers the next visual stimulus.

An advantage of this embodiment is that the subject is unaware that by resting the marking hand 100 on the platform 120, he effectively signals the software that a visual stimulus may be triggered. Therefore, by releasing the subject from the requirement to actively trigger the visual stimulus, this method enables the subject to allocate most of his attention resources to the touch screen task.

It is noted that while the hand position monitoring unit 116 of FIG. 3A-3B is implemented using a plurality of switching devices connected in series to each other any other suitable switching arrangement known in the art may also be used. For example, the hand position monitoring unit 116 may be implemented by using a single switch 140 in the circuit 145.

Figure 4A:
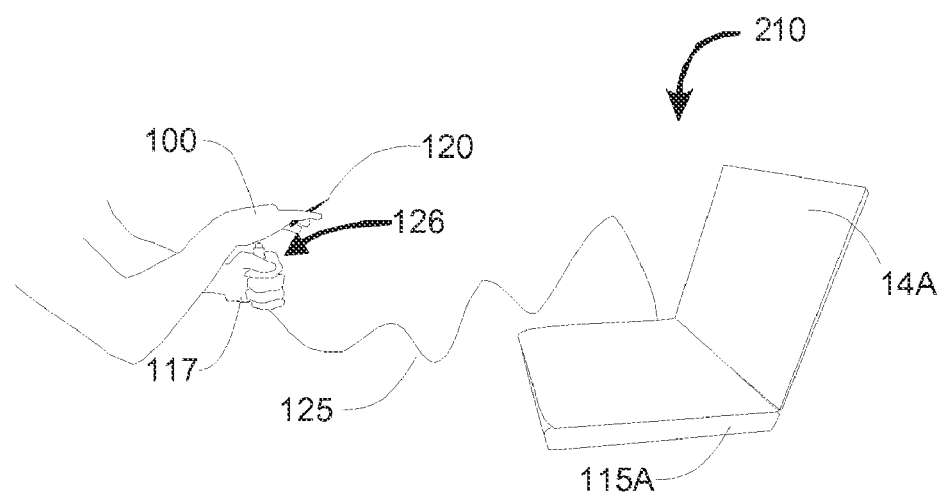
FIGS. 4A-4C are schematic isometric views illustrating different hand positions of a subject using a subject held hand position monitoring unit in accordance with another embodiment of the present invention.
Figure 4B:
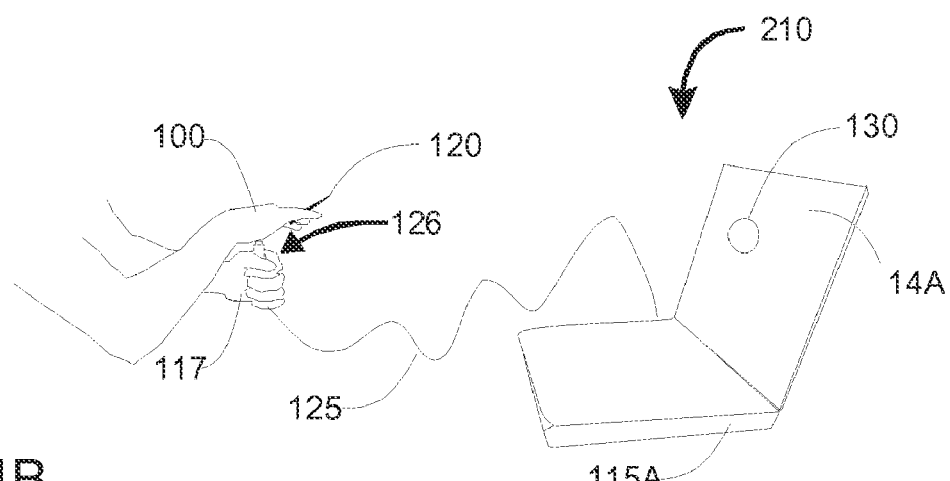
Figure 4C:
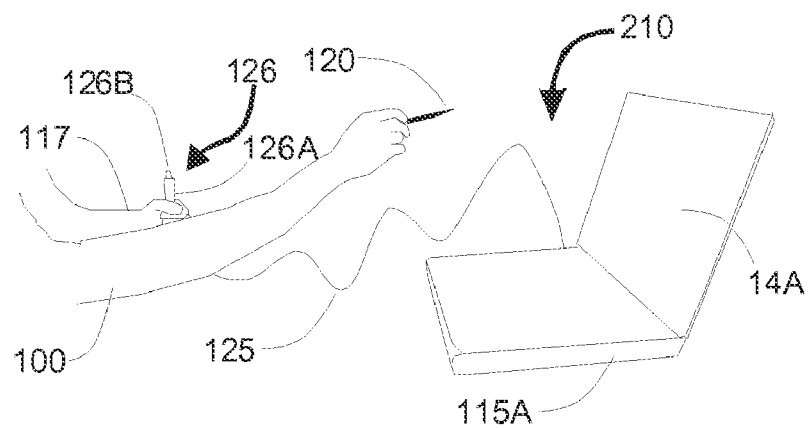

Reference is now made to FIGS. 4A-4C which are schematic isometric views illustrating different hand positions of a subject using a subject held hand position monitoring unit in accordance with another embodiment.

The System 210 includes a computer 115A having a touch sensitive display screen 14A. The system 210 also includes a hand held switching unit 126. The hand held switching unit 126 includes a handle 126A, a switching button 126B and a connecting cable 125. The handle 126A may be any suitable type of handle made from plastic or any other suitable material and shaped to be conveniently held by the hand of a subject. The switching button 126B may be any type of button suitably coupled to a switching mechanism (not shown for the sake of clarity of illustration). The switching mechanism is suitably electrically coupled to suitable electrical conducting wires (not shown in detail) which are included in the connecting cable 125. The connecting cable 125 may by suitably connected to the computer 115A through a suitable output interface or connector (not shown). The connector may be but is not limited to, a USB connector, a PS/2 Connector, an IEEE 32 parallel connector or any other suitable connector known in the art. If the switching mechanism is of the pushbutton switch type, when the switching button 126B is pressed the electrical circuit is either opened or closed. In this way the program running on the computer 115A may receive a signal (such as, for example, a certain current level or a zero current) indicating whether the button 126B has been pressed.

In operation, the marking hand 100 of the tested subject, which may (optionally) hold a stylus pen 120, presses on the switching button 126B of the handle 126A held by the non-marking hand 117 of the subject. In this position, the marking hand 100 does not obstruct the visual field of the subject. When the switching button 126B is pressed, the switching mechanism is activated and this closes an electrical circuit (not shown in detail for the sake of clarity of illustration) connected to the computer 115A. This signals the program running on the computer 115A that the marking hand 100 does not obstruct the visual field of the subject, and that a visual stimulus may be triggered. In FIG. 4B, a visual stimulus 130 is displayed on the touch sensitive display screen 14A of the computer 115A. In FIG. 4C, the marking hand 100 responds to the stimulus 130 by releasing the switching button 126B and moving towards the touch sensitive display screen 14A for marking a location on the touch sensitive display screen 14A with the (optional) stylus pen 120. The releasing of the switching button 126B signals to the computer 115A that the subject may be in the process of making a response, and that the marking hand 100 may (possibly) be obstructing the visual field of the subject. In this condition the program waits until the subject presses again with his marking hand 100 on the switching button 126B of the hand position monitoring unit 126, indicating that the marking hand has been returned to a position which does not obstruct the filed of view of the subject and that the subject has completed the marking response. Once the switching button 126B has been pressed, the program running on the computer 115A may initiate the presentation of another stimulus on the touch sensitive display screen 14A (if the test has not been finished yet).

It is noted that the switching mechanism connected to the switching button 126B may be any suitable switching mechanism known in the art, such as but not limited to, a electro-mechanical switching mechanism, an electro optical switching mechanism, a magnetic switching mechanism and any other suitable type of switching device known in the art. The switching mechanism may be a pushbutton type switch, a latching switch, or any other suitable type of switch, known in the art. The person skilled in the art will appreciate that many types of switching arrangements, switching mechanisms, and methods for processing the signals output by the hand position monitoring unit 126 may be implemented as is well known in the art, all such combinations and variations of switching mechanisms, switching methods and signal processing methods may be easily implemented by the person skilled in the art without undue experimentation and are included within the scope of the present disclosure. Similarly, the precise signaling method may use a current signal, a voltage signal or any other suitable type of signaling known in the art.

Among the advantages of using a hand held hand position monitoring unit as disclosed hereinabove is that usually, finding one's hand with the other hand is an intrinsic ability that does not require vision. Therefore, while triggering the visual stimulus is done by an active action of the subject, this embodiment allows the subject not to lose, at any time, visual contact with the touch sensitive display screen which may improve the test performance of the subject.

It is noted that when switching unit(s) are used to signal the position of the marking hand 100 of the subject, the position of such switching unit(s) need not necessarily be limited to a position close to the body of the subject.

Figure 5:
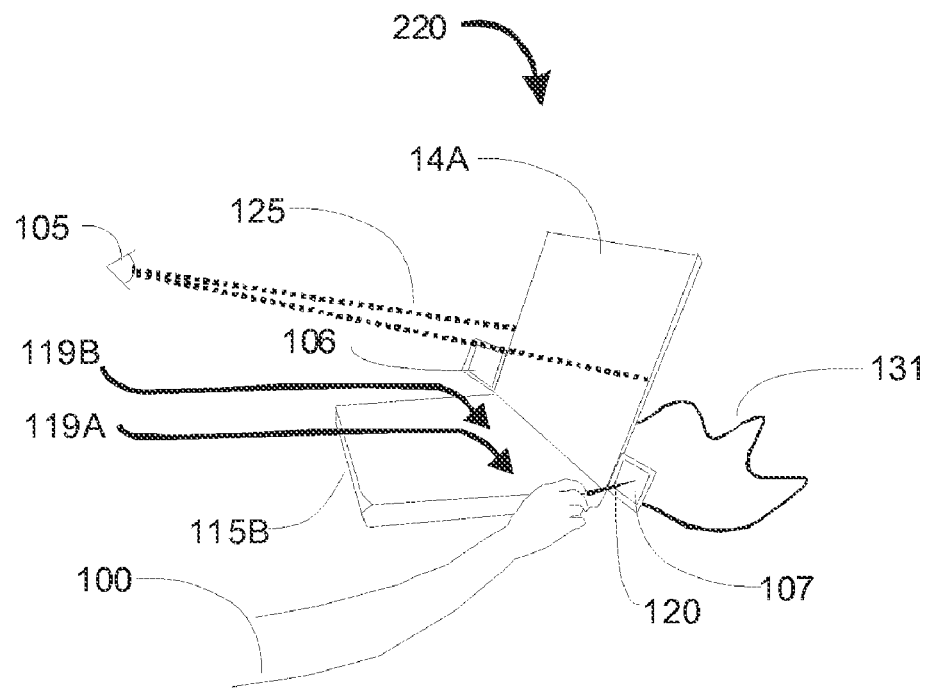
FIG. 5 is a schematic isometric view illustrating a system including hand position monitoring unit(s) for performing a touch screen task, in accordance with another embodiment of the present invention.

Reference is now made to FIG. 5 which is a schematic isometric view illustrating a system including hand position monitoring unit(s) for performing a touch screen task, in accordance with another embodiment of the present invention.

The System 220 includes a computer 115B having a touch sensitive display screen 14A. The system 220 also includes two switches 106 and 107 that are attached to either side of the touch screen 14A. The switches 106 and 107 may be push-button switches but may also be mechanical, electrical or optical switches of any suitable type known in the art. The subject (not fully shown) uses the marking hand 100 to activate the right switch 107 (for a right-handed subject) by touching or pressing the switch 107, or the left switch 106 (for a left-handed subject) to trigger the displaying of a visual stimulus on the touch sensitive screen 14A. The switches 106 and 107 may be connected via an electrical circuit 131 to a port of the computer. When a right-handed (or left-handed) subject activates the right switch 107 (or the left switch 106), the marking hand 100 does not obstruct the visual field, and a visual stimulus may be effectively triggered.

The operation of the switch 106 or 107 is similar to the operation of the hand position monitoring unit 126 as described in detail hereinabove.

It will be appreciated by those skilled in the art that it is not obligatory to use two (left and right switches) in the system 220. For example, if the computer 115B is a laptop computer (as shown in FIG. 5) or if it is a desktop personal computer which are being used by a single person, only one of the switches 106 and 107 (the left or the right switch) may be attached to the screen 14A depending on whether the user is right handed or left handed.

It is noted that while the switch or switches (106 and/or 107) are shown as attached to the screen 14A, many variations and permutations may be possible. For example, the switch (es) 106 and/or 107 may be detachably attached switches which may be attached to and removed from the screen 14A (or, alternatively, to other suitable parts of the computer 115B), it may also be possible to permanently attach one or more of the switches 106 and/or 107 to the computer 115B. Such detachable attachment configurations may be implemented by using suitable glue stickers or Velcro® pieces or any other suitable means for detachably attaching a switch to a screen or to another suitable part of the computer 115B, as is known in the art. Alternatively, the switch(es) 106 and/or 107 may be implemented as an integral part of the screen 14A and/or as an integral part of any other suitable part of the computer 115B.

In another embodiment it is also possible to attach the switch or switches to the portions of the housing of the computer 115B labeled by the arrows 119A and 119B (or to any other suitable part(s) of the computer 115B).

Figure 6:
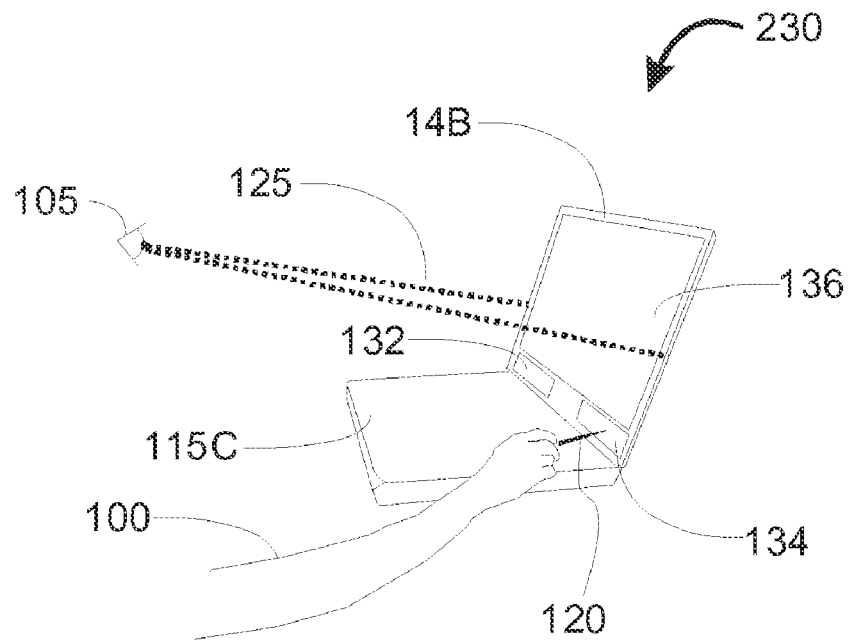
FIG. 6 is a schematic isometric view illustrating a system including hand position monitoring unit(s) for performing a touch screen task, in accordance with another embodiment of the present invention.

Reference is now made to FIG. 6 which is a schematic isometric view illustrating a system including hand position monitoring unit(s) for performing a touch screen task, in accordance with another embodiment.

The system 230 includes a computer 115C with a program for running visual tasks similar to that described by the other embodiments above. The computer 115C includes a touch screen 14B which includes two designated areas 132 and 134 thereon.

In operation, the subject triggers the presentation of a visual stimulus by marking on the touch screen 14B in a designated area (either in the designated area 132 for a left handed subject or in the designated area 134 for a right handed subject), such that the marking hand 100 does not obstruct the visual field 125 of the subject's tested eye 105. In this embodiment, the touch screen 14B may be logically divided into a stimulus/response area 136 and a triggering area 134 (for a right-handed subject) or 132 (for a left-handed subject). To trigger a visual stimulus, the subject marks (touches with his marking hand 100 or with the stylus pen 120 held by the marking hand 100) the touch screen 14B on the designated triggering area 134 or 132 (depending on whether he is right- or left-handed, respectively). The visual stimulus is then presented on the stimulus/response area 136. The triggering areas 132 and 134 are positioned on the screen 14B such that when the subjects hand is touching or marking one of them, the marking hand does not obstruct the visual field 125 of the subject thus enabling effective displaying of the visual stimulus.

It is noted that while in the embodiment illustrated in FIG. 6 the triggering areas 132 and 134 are logically defined (and may thus be modified with respect to their location on the touch screen 14B and their size by suitable programming or menus of the software installed in the computer 115C) on the touch screen 14B by suitable programming of the computer 115C, it may also be possible, in accordance with another embodiment, to implement the triggering areas 132 and 134 as fixed (hard wired) areas on the touch screen 14B. In this additional embodiment, the triggering areas 132 and 134 are dedicated for use as a triggering area only. For example, the fixed triggering areas 132 and 134 may be implemented in a similar way in which certain screen areas are dedicated to perform specific input functions in commercially available personal digital assistant (PDA) devices, as is known in the art.

It is further noted that, in accordance with yet another embodiment, the designated triggering area may be implemented as a single designated trigger area (not shown in FIG. 6) positioned in the center of the lower region of the touch screen 14B. Such a single designated trigger region may be used by both right handed and left handed subjects, provided that the size of the screen and the positioning and size of the single triggering area are designed as to prevent blocking of the field of view 125 when the marking hand 100 of the subject is touching or marking the single triggering area.

Figure 7A:
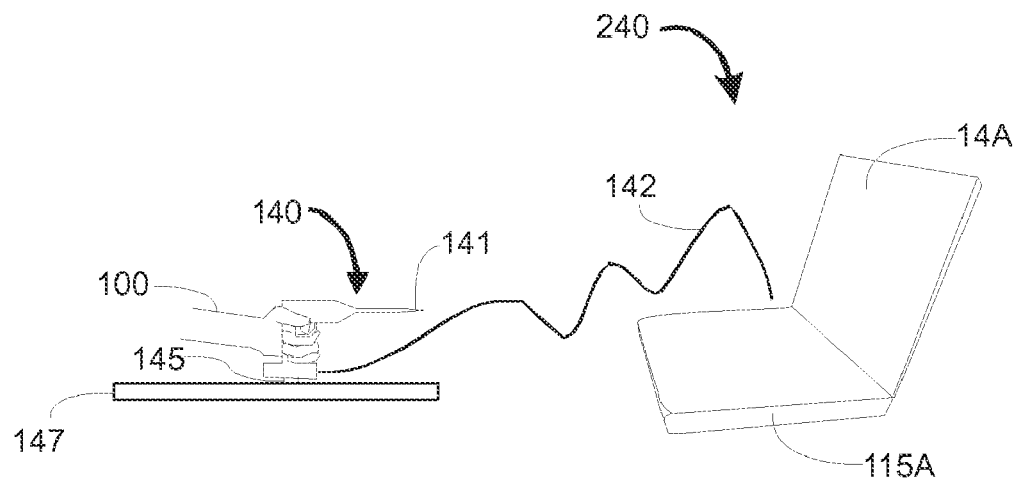
FIGS. 7A-7B are schematic diagrams illustrating a system including a hand position monitoring unit for performing a touch screen task which also functions as a marking device, in accordance with another embodiment of the present invention.
Figure 7B:
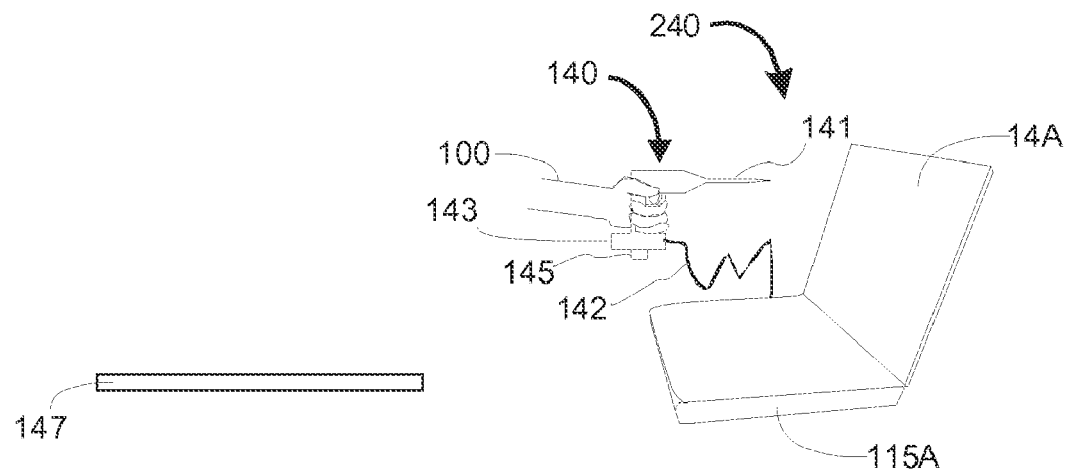

Reference is now made to FIGS. 7A-7B which are schematic diagrams illustrating a system including a hand position monitoring unit for performing a touch screen task which also functions as a marking device, in accordance with yet another embodiment.

The system 240 includes a computer 115A having a touch sensitive screen 14A as described in detail hereinabove. The system 240 also includes a combined marking/positioning unit 140 and a hand rest platform 147. The positioning/marking unit 140 may be shaped like a "hand gun" or pistol (as illustrated in the non-limiting example illustrated in FIGS. 7A-7B) or may have any other convenient shape for holding in the marking hand 100 of the subject. The positioning/marking unit 140 has a hand held portion 143 adapted for being held by the marking hand 100 and an elongated marking portion 141 that may be used to make a marking on the touch screen 14A. A suitable switch 145 is included in the base of the hand held portion 143. The hand held portion 143 also includes an output cable 142 connecting the switch 145 to a suitable input interface of the computer 115A. The switch 145 may be a pushbutton switch but may also be implemented as any other suitable type of switch known in the art. In operation, the subject holds the positioning/marking unit 140 in the marking hand 100 and places it on the rest platform 147. When the switch 145 gets pressed to the rest platform 147, the cable 142 may provide a signal to the computer 115A indicating that the marking hand 100 is positioned on the rest platform 147 and that it does not obstruct the field of view of the tested eye of the subject. The program may then present a stimulus on the touch screen 14A.

Turning to FIG. 7B, when the subject raises the positioning/marking unit 140 to make a marking on the touch screen 14A, the positioning/marking unit 140 leaves the rest platform 147, the switch 145 is released and the signal to the computer 115A is turned off, signaling to the program installed in the computer 115A that the subject may be in the process of making a response, and that the marking hand 100 may (possibly) be obstructing the visual field of the subject. The program will therefore not present a new stimulus to the subject until the subject places the positioning/marking unit 140 again on the rest platform 147 such that the switch 145 gets pressed against the surface of the rest platform and provides the appropriate signal to the computer 115A.

Figure 8:
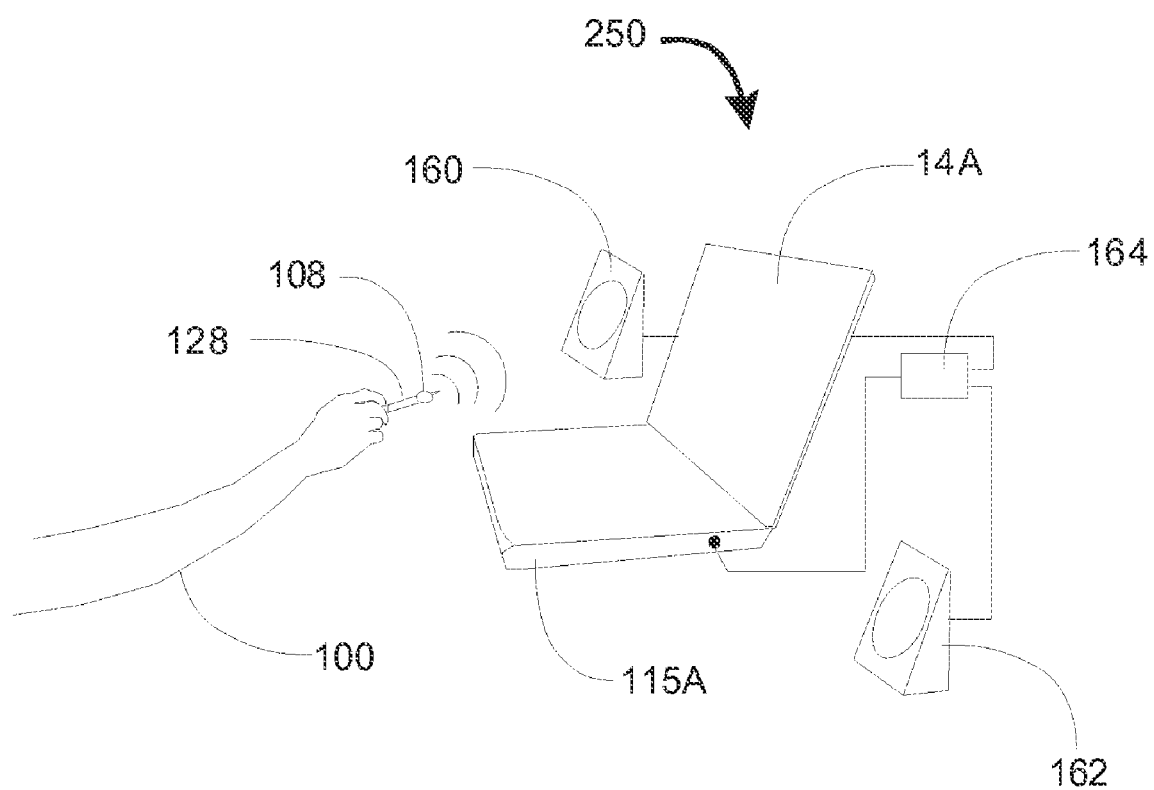
FIG. 8 is a schematic isometric view illustrating a system including an ultrasonic hand position monitoring unit for performing a touch screen task, in accordance with another embodiment of the present invention.

Reference is now made to FIG. 8 which is a schematic isometric view illustrating a system including an ultrasonic hand position monitoring unit for performing a touch screen task, in accordance with still another embodiment.

It system 250, the location of the marking hand 100 is monitored based on E-Pos technology (an additional explanation of the technology is available at the following world wide web link http://www.cpos-ps.com/inr.asp?pid=1311&ppid=1312). An ultrasonic transmitter 108 is embedded within or attached to a stylus pen 128 held by the marking hand 100. Two ultrasonic receivers 160 and 162 positioned on the two sides of the touch screen 14A continuously acquire ultrasonic signals broadcasted from the ultrasonic transmitter 108. An A/D converter unit 164 digitizes the analog signals received by the receivers 160 and 162 and feeds the digitized data to the computer 115A via a suitable digital interface (for example, using a USB input socket, an RS-232 Socket, or any other suitable connecting interface as is known in the art). By using triangulation techniques, the program installed on the computer 115A calculates the 3-D position of the ultrasonic transmitter 108, and infers from this information the approximate position of the marking hand 100 in real time. The program synchronizes the presenting of the visual stimulus to a time when the marking hand 100 is positioned such that it does not obstruct the visual field (not shown) of the subject.

Figure 9A:
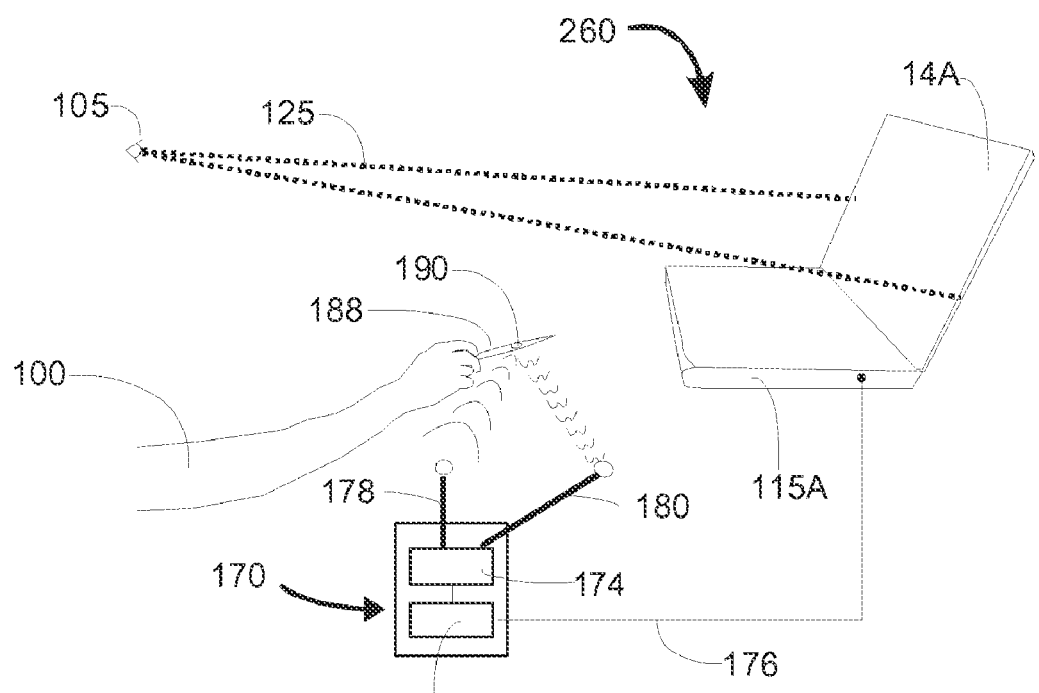
FIGS. 9A and 9B are schematic isometric views illustrating a system including an RFID based hand position monitoring unit for performing a touch screen task, in accordance with another embodiment of the present invention.
Figure 9B:
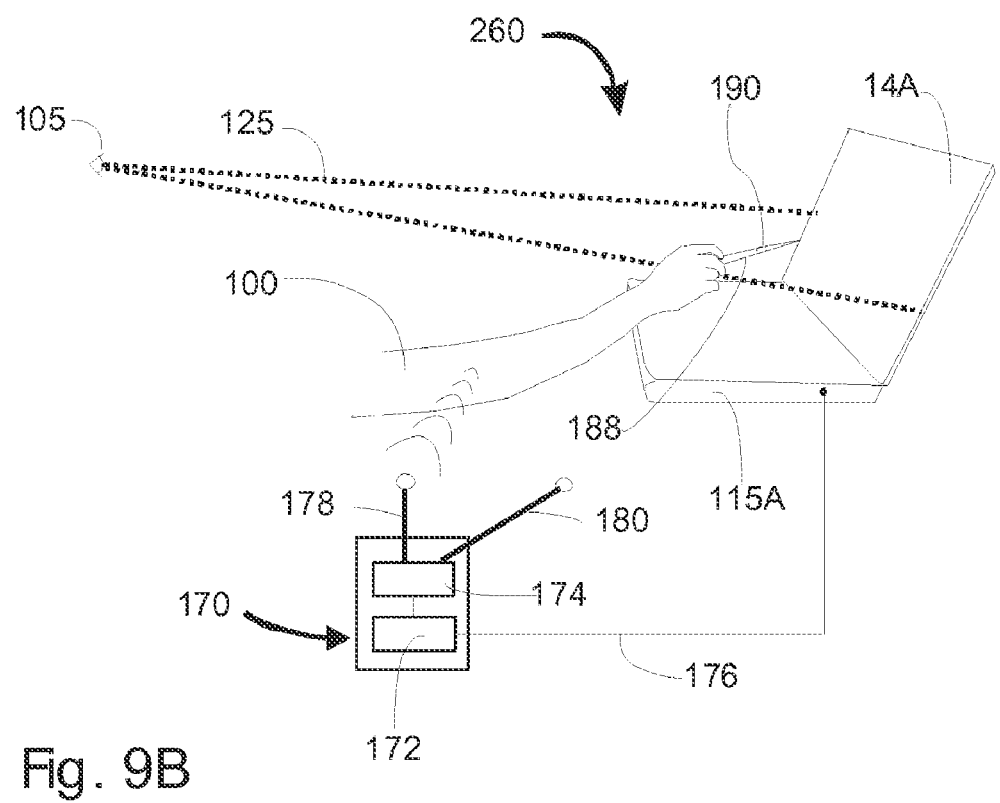

Reference is now made to FIGS. 9A and 9B which are schematic isometric views illustrating a system including an RFID based hand position monitoring unit for performing a touch screen task, in accordance with a further embodiment.

A system 260 includes the computer 115A having a touch sensitive screen 14A as disclosed hereinabove. The system 260 also includes a radio-frequency identification (RFID) interrogating unit 170 suitably coupled to the computer 115A by a signal cable 176. The RFID interrogating unit 170 includes a transceiver unit 174, a decoder unit 172, a transmitting antenna 178 and a receiving antenna 180. The marking hand 100 of the subject holds a stylus pen 188. The stylus pen 188 includes an active or a passive RFID tag 190 attached thereto or embedded therein. The transceiver unit 174 continuously emits an electromagnetic wave. In FIG. 9A, the RFID tag 190 is held by the marking hand 100 within range of the transmitting antenna 178, and the electromagnetic wave powers up a microchip unit (not shown in detail) within the RFID tag 190. The activated microchip unit modulates the electromagnetic wave that bounces back from the RFID tag 190 to the receiving antenna 180. The modulated electromagnetic wave is decoded by the decoder 172, and if it fits a predefined pattern the decoder unit 172 transmits an electrical signal to the computer 115A. This signal indicates to the program installed on the computer 115A that the marking hand 100 is in the proximity of the interrogating unit 170, and therefore that the marking hand 100 does not obstruct the visual field 125 extending from the tested eye 105 to the touch screen 14A. The program may then trigger the presenting of a visual stimulus on the touch screen 14A. In FIG. 9B, the RFID tag 190 is not within the range of the transmitting antenna 178, and the microchip unit within the RFID tag 190 is therefore not activated. The receiving antenna 180 therefore does not acquire the characteristically modulated electromagnetic wave, and the computer 115A does not receive the electrical signal from the decoder unit 172. This indicates to the program that the marking hand 100 may (possibly) obstruct the visual field 125 of the subject, and therefore the presentation of a visual stimulus is not triggered.

Figure 10A:
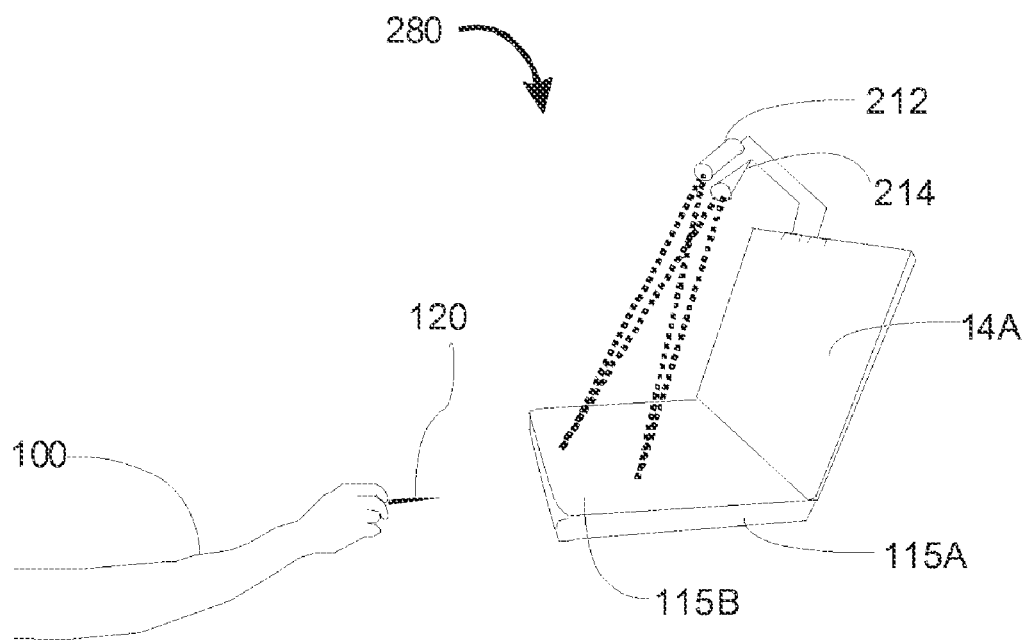
FIGS. 10A and 10B are schematic isometric views illustrating a system including an infa-red proximity sensing based hand position monitoring unit for performing a touch screen task, in accordance with another embodiment.
Figure 10B:
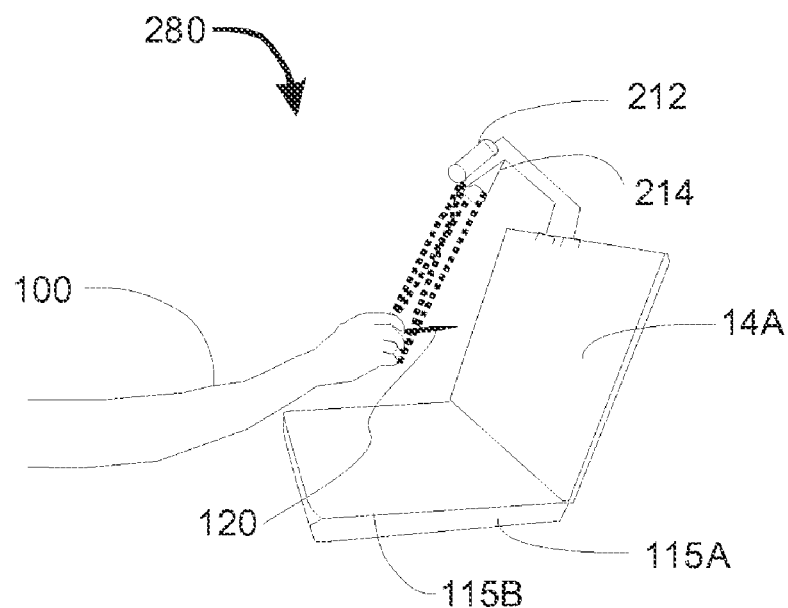

Reference is now made to FIGS. 10A and 10B which are schematic isometric views illustrating a system including an infra-red proximity sensing based hand position monitoring unit for performing a touch screen task, in accordance with another embodiment.

In the system 280, the location of the marking hand is monitored with a proximity sensor based on detection of infra-red waves emitted by warm bodies such as the marking hand 100 of the subject. The system 280 includes the computer 115A having a touch sensitive screen 14A as disclosed hereinabove. The system 260 also includes an Infra-red (IR) electromagnetic radiation source 212, such as, but not limited to an IR light emitting diode (LED), and an IR electromagnetic radiation detector 214 such as, for example, a suitable IR sensitive photo-detector, phototransistor, photodiode, photogate, and the like as is known in the art. The IR radiation source 212 and the IR radiation detector 214 are suitably coupled to the computer 115A (connections are not shown in FIGS. 10A and 10B for the sake of clarity of illustration) or to a suitable electronic circuit (not shown) or to an extension card (not shown) installed in the computer 115A, for suitably operating the IR radiation source 212 and the IR radiation detector 214.

The IR LED 212 located on top of the touch screen 14A emits infra-red radiation at a specific given frequency (or within a specific known frequency range). The beam emitted by the IR LED 212 crosses the visual field extending from the tested eye (not shown) to the touch screen 14A. An IR detector 214 located on top of the touch screen 14A detects infra-red waves in the vicinity of the IR detector 214. In FIG. 10A, the marking hand 100 is distant from the IR detector 214 and therefore the only infra-red radiation sensed by the IR detector 214 is the radiation emitted by the IR LED 212 and reflected from the surface 115B of the computer 115A which is identifiable by having a specific signature with respect to the intensity of radiation and the frequency range. This received IR signature is interpreted by the program installed on the computer 115A to mean that the marking hand 100 is not positioned near the touch screen 14A and is therefore not blocking the visual field of the subject. The program may thus trigger the presentation of a visual stimulus on the touch screen 14A.

In FIG. 10B the marking hand 100 is illustrated as making a response and is approaching the touch screen 14A. The marking hand 100 emits infra-red radiation at a frequency range different than the frequency range of the IR LED 212 which is detected by the IR detector 214, together with the infa-red waves emitted by the IR LED 212 and reflected from the from the surface 115B of the computer 115A and from the hand 100, that are also detected by the IR detector 214. This composite signal, when fed to the computer 115A and processed, provides an IR signature which is different than the IR signature obtained when the hand 100 is not positioned near the touch screen 14A. The different received IR signature indicates to the program installed on the computer 115A that the subject is making a response and that the hand 100 is close to the touch screen 14A and may therefore possibly block the visual field of the subject. The program therefore avoids the presentation of a visual stimulus until the IR signature changes to an acceptable signature. The signature may be compared to predetermined template signatures which were factory present or alternatively generated in a patient specific system training session which collects data for each specific patient or subject in which case the signatures are more accurate as they are based on actual measurements obtained for each subject.

Figure 11A:
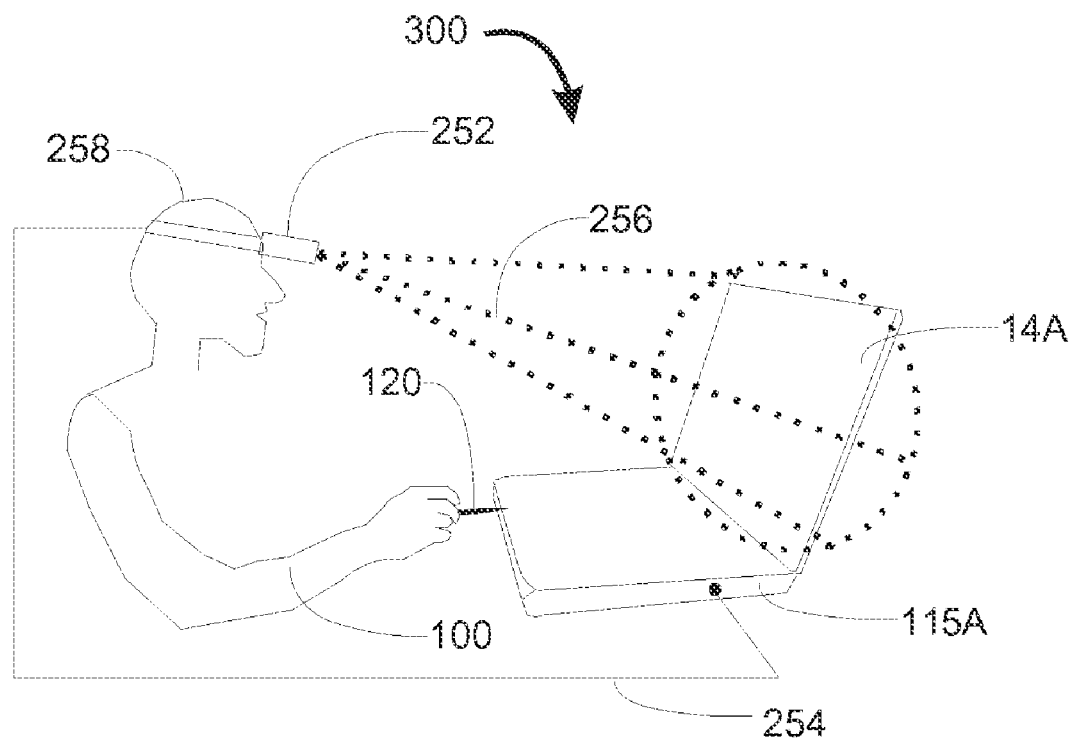
FIGS. 11A and 11B are schematic isometric views illustrating a system including a motion detector device attached to the subject for monitoring hand position to control the performing of a touch screen task, in accordance with another embodiment of the present invention.
Figure 11B:
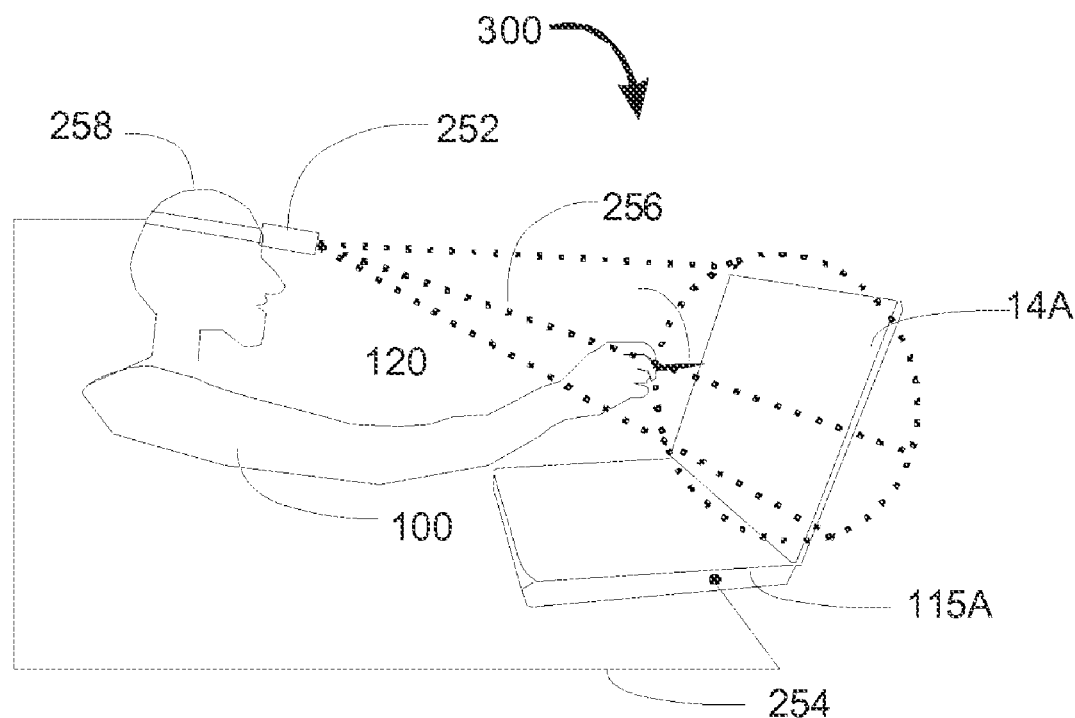

Reference is now made to FIGS. 11A and 11B which are schematic isometric views illustrating a system including a motion detector attached to the subject for monitoring hand position to control the performing of a touch screen task, in accordance with another embodiment.

The system 300 includes the computer 115A having a touch sensitive screen 14A as disclosed in detail hereinabove. The system 300 further includes a motion detecting device 252 suitably attached to the head 258 of the subject (or, alternatively, under the subject's chin, or attached to any other suitable part of the subject's head 258). The motion detecting device 252 is attached to the computer 115A through a suitable connecting cable 254. The connecting cable 254 may by suitably connected to the computer 115A through a suitable output interface or connector (not shown). The connector may be but is not limited to, a USB connector, a PS/2 Connector, an IEEE 32 parallel connector or any other suitable connector known in the art. The data and/or the signals output by the motion detecting device 252 may be sent for processing by the processor included in the computer 115A, through the connecting cable 254. In operation, the motion detecting device 252 operates to detect any motion within the volume of an imaginary cone 256 that extends between the motion detecting device 252 and the touch sensitive screen 14A.

In FIG. 11A, the marking hand 100 is outside the motion detection imaginary cone 256 and the motion detecting device 252 does not detect any motion within the imaginary cone 256. The program running on the computer interprets this to indicate that there is no obstruction of the subject's field of view and enables the presentation of a visual stimulus to the subject.

In FIG. 11B the marking hand 100 enters the volume of the imaginary cone 256, and the motion detector 252 detects the motion of the hand 100. A signal representing the detection of motion in the imaginary cone 256 is then sent to the computer 115A. The program running on the computer 115A interprets this signal as indicative of the presence of a (possible) blocking of the subject's visual field by the marking hand 100 and prevents the presentation of a stimulus on the touch sensitive screen 14A.

The motion detecting device 252 may be implemented in various different ways. For example, in accordance with a first embodiment, the motion detecting device 252 may be an infra-red volume motion detector as is commonly used in intrusion detection systems and perimeter security systems, as is known in the art The motion detecting device 252 can be implemented using various different existing technologies for motion detection. For example, by using a passive infrared (PIR) sensor (not shown in detail) covered with a plastic Fresnel lens (not shown) that divides the scene into discrete optical zones (e.g., one of the "Hawkeye" series model line PIR detectors, such as, for example the model MS13A wireless Hawkeye motion sensor commercially available from X10 Wireless Technology Inc, WA, USA.). The marking hand 100 crosses the boundary that divides adjacent optical zones on a Fresnel lens included in the motion detecting device 252. As a result, the PIR sensor detects a change in the infrared signature of the hand, and produces a signal which indicates to the program installed on the computer 115A that the marking hand 100 may possibly obstruct the visual field of the subject and that a visual stimulus should not be presented on the touch sensitive screen 14A. The construction and operation of PIR motion detecting devices is well known in the art, is not the subject matter of the invention and is therefore not disclosed in detail hereinafter.

It is noted that if the model MS13A sensor is used in implementing the motion detecting device 252, the cable 254 becomes redundant as the signal representing the detection of motion may be wirelessly transmitted to a suitable receiver (not shown) suitably coupled to the computer 115A.

In accordance with another embodiment, the motion detecting device 252 may include a video camera which acquires an image of any object which enters the imaginary cone 256. The video signals (which maybe analog or digital video signals) may be received and processed by the computer 115A. The cable 254 may be implemented as a cable configured for transferring a video signal to the computer 115A, and may be interfaced to the computer 115A through a suitable video signal interface including but not limited to a IEEE 1394 (Firewire) interface, USB2, S-Video interface or any other suitable type of digital or analog video signal connector or interface which may be either built in the computer 115A or may be a part of a suitable plug-in computer interface card, as is known in the art. Alternatively, the video images may be received and processed by any suitable image or data processor (not shown) which may be integrated into the motion detecting device 252.

When the motion detecting device 252 (or the program running on the processor of the computer 115A) detects the motion of the marking hand 100 which enters the cone 256 (which in this embodiment represents the collimated field of view of the video camera) the program running on the computer 115A prevents the presentation of stimuli on the touch sensitive screen 14A as explained hereinabove. When no motion is detected in the video images output by the video camera included in the motion detecting device 252, the program may present a visual stimulus on the touch sensitive screen 14A.

It will be appreciated by those skilled in the art that methods for processing a video image to detect motion or intrusion of an object in the image, are well known in the art, are not the subject matter of the present invention and are therefore not disclosed herein in detail. Many off the shelf computer programs for detecting motion in a video signal stream are commercially available and may be used for implementing the disclosed embodiment.

Briefly, in accordance with one non-limiting example, such motion detecting program continuously (or intermittently) compares the received video image to a reference image. If a threshold number of pixels have changed color relative to the reference image, the system interprets this as an intrusion of an object (for example, the marking hand 100) into the imaginary cone 256 and interprets this detected motion or intrusion as possible blocking of the field of view of the subject. When such detection of motion occurs, the system 300 avoids the presenting of a stimulus on the touch sensitive screen 14A. However, it is noted that any other suitable type of method, program or algorithm for motion or intrusion detection known in the art may be used or adapted for use in the system 300.

It is noted that while different embodiments have been disclosed using one or more switching devices (switches), many other configurations of other embodiments may employ various different types of sensor(s) or sensor combinations for sensing and/or monitoring and or detecting the position of the marking hand of the subject and/or. Such sensors may include, but are not limited to mechanical sensors, magnetic sensors, capacitive sensors, proximity sensors, passive or active motion sensors, intrusion detecting sensors, electro-optical sensors, electromechanical sensors, electromagnetic sensors, infra-red sensors, microwave sensors, Doppler radar based sensors, magnetostrictive material based sensors and the like, as is known in the art It will be appreciated by those skilled in the art that while some of the embodiments disclosed hereinabove and illustrated in the drawings use suitable electrical conductors and/or cables to connect sensors and or switches to the computer included in the various disclosed systems, the scope of the embodiments is also intended to include implementations in which the sensors and/or the switches and/or the motion detecting devices are wirelessly coupled to the computer of the system by any suitable wireless coupling method as is known in the art. This may be performed by using, inter alia, IR wireless transceivers, ultrasonic wireless transceivers, RF transceivers, Bluetooth wireless transceivers, or any other suitable wireless communication technology or method known in the art.

It is further noted that the number, configuration, and positioning of the switching devices and/or sensors and/or motion detecting and/or intrusion detecting devices used for implementing the various embodiments are not limited to what is described hereinabove and illustrated in the drawings and may be varied and modified in accordance with various design considerations, as will be easily understood and implemented by those skilled in the art.

What is claimed is:

1. A system for delivering a touch sensitive screen task to a subject, the system comprising:
   a touch sensitive display unit for presenting visual stimuli to a subject and for providing responses of said subject to at least some of said visual stimuli, wherein said subject's view of said touch sensitive display unit is at least partially blocked by a hand of said subject while said subject indicates a response on said touch sensitive display unit;
   at least one hand position monitoring unit to be engaged by said hand of said subject while said subject is not indicating a response, said hand position monitoring unit being locatable relative to said touch sensitive display unit such that said hand does not block any portion of said touch sensitive display unit from said subject's view while said hand is engaging said hand position monitoring unit, and said hand position monitoring unit providing output signals indicating whether said hand position monitoring unit is engaged by said hand; and
   a controller/processor unit operatively coupled to said touch sensitive display unit and to said at least one hand position monitoring unit for receiving said output signals from said at least one hand position monitoring unit and for processing at least said output signals to control the displaying of said visual stimuli on said touch sensitive display unit;
   wherein said visual stimuli correspond to a visual test;
   wherein said controller/processor unit is configured to pause a visual stimulus for allowing said subject to indicate said response when said at least one hand position monitoring unit is not engaged by said hand, and said controller/processor unit is configured to cause a subsequent visual stimulus to be displayed when said hand of said subject is returned to engage said at least one position monitoring unit.

2. The system according to claim 1 wherein said at least one hand position monitoring unit is selected from a mechanical hand position monitoring unit, an electromechanical hand position monitoring unit, an ultrasonic hand position monitoring unit, a stationary switching unit, a hand held switching unit, a switching mechanism, an electromechanical switching mechanism, an electro-optical switching mechanism, a magnetic switching mechanism, an optical switch, an infra-red proximity sensing based hand position monitoring unit, a mechanical sensor, a magnetic sensor, a capacitive sensor, a proximity sensor, an intrusion detecting sensor, an electro-optical sensor, an electromechanical sensor, an electromagnetic sensor, an infra-red sensor, a microwave sensor, and any combinations thereof.

3. The system according to claim 1 wherein said at least one hand position monitoring unit comprises at least one switch, said at least one switch is selected from a pushbutton switch, a latching switch, an optical switch, an electro-optical switch, a mechanical switch, an electromechanical switch, a magnetic switch and any combinations thereof.

4. The system according to claim 1 wherein said at least one hand position monitoring unit comprises two hand position monitoring units comprising a first hand position monitoring unit usable for monitoring the position of the right hand of a right handed user and a second hand position monitoring unit usable for monitoring the position of the left hand of a left handed user.

5. The system according to claim 1 wherein said output signals of said at least one hand position monitoring unit are communicated to said controller/processor unit by communicating means selected from communication wires for connecting said at least one hand position monitoring unit and said controller/processor unit and wireless communication devices.

6. The system according to claim 5 wherein said wireless communication devices are selected from wireless transmitters, wireless receivers, wireless transceivers, IR wireless transmitters, infra-red wireless receivers, infra-red transceivers, ultrasonic wireless transmitters, ultrasonic wireless receivers, ultrasonic wireless transceivers, radio-frequency receivers, radio frequency transmitters, radio frequency transceivers, Bluetooth wireless receivers, Bluetooth wireless transmitters, Bluetooth wireless transceivers and any combinations thereof.

7. The system according to claim 1 wherein said hand position monitoring unit comprises a platform and said hand position monitoring unit provides an output signal when said hand of said subject is positioned on said platform.

8. The system according to claim 1 wherein said controller/processor unit is configured for presenting said visual stimuli to said subject upon receiving said output signals.

9. A method for controlling the delivering of visual stimuli to a subject, the method comprising the steps of:
   presenting to said subject visual stimuli on a touch sensitive display unit;
   receiving from said subject, through said touch sensitive display unit, signals representing responses of said subject to at least some of said visual stimuli, wherein said subject uses a hand to indicate said responses;
   providing a passive hand position monitoring unit for passive engagement by relaxation of said hand of said subject while said subject is not indicating a response through said touch sensitive display unit, said hand position monitoring unit being located such that said hand of said subject does not block any portion of said touch sensitive display unit from said subject's view while said hand is engaging said hand position monitoring unit;

receiving output signals from said hand position monitoring unit indicating that said hand of said subject is presently engaging said hand position monitoring unit; and
processing at least said output signals to control timing of presenting said visual stimuli to said subject;
wherein said visual stimuli correspond to a visual test.

10. The method according to claim 9 wherein said visual stimuli are presented to said subject upon receiving said output signals.

11. The method according to claim 9 wherein said position signals are output by at least one hand position monitoring unit selected from a mechanical hand position monitoring unit, an electromechanical hand position monitoring unit, an ultrasonic hand position hand position, a stationary switching unit, a hand held switching unit, a switching mechanism, an electromechanical switching mechanism, an electro-optical switching mechanism, a magnetic switching mechanism, an optical switch, an infra-red proximity sensing based hand position monitoring unit, a mechanical sensor, a magnetic sensor, a capacitive sensor, a proximity sensor, an intrusion detecting sensor, an electro-optical sensor, an electromechanical sensor, an electromagnetic sensor, an infra-red sensor, a microwave sensor, and any combinations thereof.

12. The method according to claim 9 wherein said output signals are selected from wirelessly received position signals and position signals received through wires.

13. The method according to claim 9 wherein said subject chooses to use either a left hand or a right hand to indicate said responses.

14. The method according to claim 9 wherein said hand position monitoring unit includes a platform on which said hand of said subject rests between responses.

15. The method according to claim 9 wherein said hand position monitoring unit includes a switching mechanism intentionally activated by said hand of said subject.

16. A method for controlling the delivering of visual stimuli to a subject, the method comprising the steps of:
presenting to said subject a visual stimulus on a touch sensitive screen;
pausing said visual stimulus in response to receiving a signal indicating that the subject is using a hand to indicate a response to said visual stimulus;
receiving a signal indicating that the subject has indicated said response to said visual stimuli by touching said touch sensitive screen;
receiving a signal indicating that said hand of the subject does not block the subject's view of said touch sensitive screen; and
presenting to said subject a next visual stimulus only after receiving said signal indicating that said hand of the subject does not block the subject's view of said touch sensitive screen;
wherein said visual stimulus corresponds to a visual test.

* * * * *